United States Patent [19]

Mochizuki et al.

[11] 4,059,523
[45] Nov. 22, 1977

[54] COLUMN FOR USE IN HIGH SPEED LIQUID CHROMATOGRAPHY

[75] Inventors: Koichi Mochizuki; Shigeho Hiragaki, both of Hachioji, Japan

[73] Assignee: Japan Spectroscopic Co., Ltd., Tokyo, Japan

[21] Appl. No.: 725,938

[22] Filed: Sept. 23, 1976

[51] Int. Cl.² ............................................. B01D 15/08
[52] U.S. Cl. .............................. 210/198 C; 210/31 C; 210/350
[58] Field of Search ................. 210/31 C, 198 C, 350; 55/67, 197, 386

[56] References Cited

U.S. PATENT DOCUMENTS

| | | | |
|---|---|---|---|
| 2,988,222 | 6/1961 | Hagdahl | 210/350 |
| 3,005,514 | 10/1961 | Cole et al. | 55/386 |
| 3,180,825 | 4/1965 | Couvreur et al. | 210/350 X |
| 3,866,308 | 2/1975 | Halasz et al. | 210/198 C |
| 3,878,092 | 4/1975 | Fuller | 210/31 C |

OTHER PUBLICATIONS

The Condensed Chemical Dictionary by Hawley, Van Nostram Reinhold Co., New York, N. Y., p. 208 1971.
Modern Practice of Liquid Chromatography—Edited by Kirkland; John Wiley & Sons, New York, N. Y., pp. 40-53.
High Speed Liquid Chromatography with Controlled Surface Porosity Supports—by Kirkland, Journal of Chromatography Science, vol. 7, Jan. 1969, pp. 7 and 11.

*Primary Examiner*—John Adee
*Attorney, Agent, or Firm*—Browdy and Neimark

[57] ABSTRACT

A column used for high speed liquid chromatography which is characterized in (a) eminent separating ability suitable for microanalysis while having a small internal diameter, (b) minimizing the separation impediment due to minute flaws, tiny recesses or the like on the inner surface thereof, and (c) facilitating packing operation of particulate packing or support material thereinto, by enabling the material to closely contact not only with each other but also with the inner surface of the column that can yield to a necessary extent.

5 Claims, 2 Drawing Figures

COLUMN FOR USE IN HIGH SPEED LIQUID CHROMATOGRAPHY

BACKGROUND OF THE INVENTION

In a chromatography, particularly in a high speed liquid chromatography, the internal diameter of the column has been required to become smaller and smaller because of increasing the separation rate, raising the microanalytic ability, enhancing the separating capacity, economizing the packing material and so on. Attempts of diminishing the internal diameter have been considerably advanced as far as practical use of columns having the internal diameter around 2.5 mm. However, further reduction of the dimension down to 1.0 mm or 0.5 mm has been hampered by the occurrence of the undermentioned disadvantages; in other words, effective reduction of the internal diameter has been, in fact, stalled.

a. The packing material packed inside the chromatographic column, usually particulate or solid layer, is stuffed in relatively close contact with almost uniform clearances between the particles, as shown in FIG. 1, but with some irregular or fairly large clearances, in relation to the inner surface of the column, which are called voids in this case. Although the clearances between the particles are nearly uniformly narrow or small, those voids between the particles located radially outermost and the inner surface of the column tend to be irregular or relatively large as shown with 3 in FIG. 1, which makes the passing rate of the eluent irregular or changeable and, in turn, conspicuously degrades the separating ability. The undesirable effect of the latter voids varies with the proportion between the column internal diameter and the particle size of the packing material; and it has been found that the decreasing of the column internal diameter below a certain value with respect to a certain value of the particle size of the packing material shows a critical degradation of the column function. This seems to be the greatest reason of preventing the reduction of the column internal diameter to below 1.0 mm. (b) The smaller the column internal diameter becomes, the greater becomes relatively the bad effect due to the minute flaws or cracks, tiny recesses or dents on the inner surface of the column, which bad effect appears in the local irregularities of the flowing speed of the liquid, consequently, in the degradation of separating ability.

This phenomenon is particularly inevitable when a particulate material of a substantially uniform particle size is used in relation to a column of a certain predetermined internal diameter. Confronting with the requirement of the gradual reduction of the column internal diameter, the above-mentioned difficulty has been a great problem to be solved. In order to alleviate the aforementioned unfavorable effect, enlarging the column internal diameter has been tried to improve the relative proportion with the particle size of the packing material, which directly contradicts the general trend of the gradual reduction of the column internal diameter and does not contribute to the solution of the problem at all.

The present invention, therefore, aims to provide a novel and practical column which has solved the difficult problem, wherein the cross-sectional area of the eluent path, even in a column having a very small internal diameter, is almost equal or uniform throughout the entire length of the column.

SUMMARY OF THE INVENTION

The present invention relates to a column for use in the high speed liquid chromatography, more particularly, to the provision of a column, having a small internal diameter, highly efficient in separating ability and suitable for microanalysis.

A primary object of this invention is to provide a novel and practical column, which is to be in close contact relationship with the packing material, constructed entirely of soft material or softenable material and packed with a packing material under pressure in such a way as to eliminate the problematical voids ordinary to the conventional columns to a state seen in FIG. 2.

Another object of this invention is to provide a novel and practical column comprising an external tube of rigid material and an internal tube of soft material, instead of the abovementioned softenable material only, in order to realize the state shown in FIG. 2 at the internal tube thereof.

DETAILED DESCRIPTION OF PREFERRED EMBODIMENTS

Figure 1:
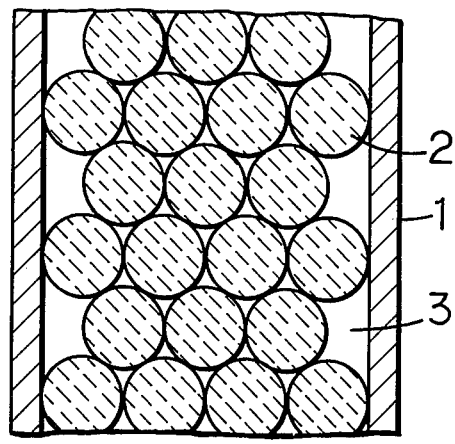
FIG. 1 is a longitudinal sectional view of a conventional column with the voids.
Figure 2:
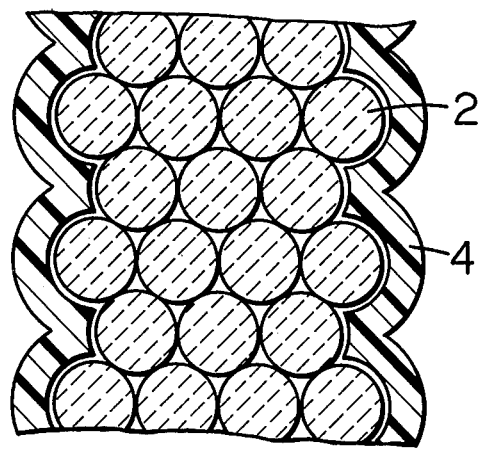
FIG. 2 is a longitudinal sectional view of a column in accordance with this invention having no voids.

As for the construction of such a column that is free from voids some preferred embodiments will be described along with the manufacturing process thereof: (a) into a stainless steel tube is inserted a tube 1 of fluoride resin or fluorocarbon resin, e.g., polytrifluorochloroethylene, followed by packing or stuffing under pressure of a packing material 2, to which are applicable all sorts of packing materials conventionally used for liquid chromatography, e.g., porous polymers, fully porous silica-gel, and etc. having a substantially uniform particle size of a sphere, as shown in FIG. 2, ranging from several tens microns to several microns ($\mu$), preferably 40 – 10 $\mu$, in other words, followed by packing or stuffing under pressure of particles made of such packing material into the tube of fluoride resin in such a way as the particles being in a close contact relationship with each other; (b) when the packing materials 2 is packed under pressure after the tube 1 of fluoride resin has been gently pre-heated to such an extent as to be slightly softened, the contact between the packing material 2 and the resin tube 1 would be even better than at a moderate temperature; (c) the tube may be made simply of the aforementioned fluoride resin without the stainless steel external tube, wherein when the packing material is packed thereinto under pressure a column of fluoride resin free from the voids can be obtained, with the external surface thereof being rugged or uneven, due to an appropriate yielding of the internal tube; and (d) packing the end portions of the column with a filter made of quartz wool or the like over a suitable length is surely preferable.

The detailed process of manufacturing the column will not be described, as it is not an essence of this invention. Since the inventors of this invention have already completed the manufacturing process thereof, an example will be cited from the Patent Application to the Japanese Patent Office No. Toku-Gan-Sho 49-72108 hereinunder. The packing material is mixed with a solvent at a predetermined ratio into a suspension, which is sucked into a soft tube of fluoride resin. Upon having securely packed a filter at the ends of the tube, the solvent is extruded out of the tube at a pressure ranging from 100 to 200 Kg/cm$^2$, leaving the packing material of solid phase in a jammed or close contact state. As a result of this process the particles of the packing material are closely contacted with each other and also with the inner surface of the tube which has yielded to be adapted thereto, as can be seen in FIG. 2, the particles being arranged in multi-layers radially extending, in a fashion that every other layer is repeatedly the same.

In the column thus obtained the particles of the packing material are packed in an externally touching relation with each other so that the clearance between the particles may be repeated with a minimum void volume or dead volume having a constant pattern. The hollow tubular body made of softenable or flexible material, when the particles of the packing material are packed under pressure to come to a close contact therewith, yields to be adapted to the shape of the particles, and eventually can be closely contacted with all the particles located on the radially outermost periphery. The yielded or transformed condition may remain as it is even after the removal of the pressure; a transformation by solidifying with cooling. The tubular body of the column, which may be a column itself or an internal tube of the column according to the situation, can be yielded or changed in form, according to the shape of the particles packed thereinto, to have a rugged or uneven external surface, which has brought about a complete elimination of large or irregular voids observed in the conventional columns.

A column comprising such a transformed hollow tubular body and the packing material, the particles of which are packed in close contact with each other and with the inner surface of the tubular body, can be practicable one for liquid chromatography only after having been packed with a filter at the open ends thereof.

The column in accordance with this invention has succeeded in preventing the irregularity of flow speed according to positions of the eluent passing therethrough, the turbulence of flowing and/or the local stagnation of flowing, by means of virtually eliminating the presence of fairly large voids 3 which might appear conventionally between the particles of the packing material and the inner surface of the tubular body of the column.

This invention enables in this way the enhancing the separating ability and the obtaining of the exact analytical results.

In concluding the description on the merits of this invention can be summed up as follows:

a. a column of high separating ability suitable for microanalysis having a small internal diameter is obtained;

b. the above column enables high speed microanalysis under high pressure with less fluid to be analyzed;

c. the soft material constituting the inner surface of the tubular body makes it easy to arrange the particles closely and regularly, which enables the diminishing of the column dimension drastically; and d. the reduction of the column size enables in turn the saving of expensive packing material, that is economizing the manufacturing cost.

It will be obvious to those skilled in the art that various changes may be made without departing from the scope of the invention and the invention is not to be considered limited to what is shown in the drawings and described in the specification.

What is claimed is:

1. A column for use in high speed liquid chromatography which is constructed by closely packing a solid phase in a hollow tubular body, said column comprising:

a solid phase wherein the composing solid particles, having a substantially uniform particle size of a sphere having a diameter less than 0.10 mm, are packed in said tubular body in close contact relationship with each other; and a tubular body having an inner diameter less than 1.0 mm, which is made of fluoro-carbon resin, and which is deformed to be adapted to the particles located at the radially outermost position, for permiting all of the particles confronting with the inner surface thereof to closely contact therewith, substantially leaving no void spaces therebetween.

2. A column for use in high speed liquid chromatography as set forth in claim 1, wherein said hollow tubular body is composed of polytrifluorochloroethylene.

3. A column for use in high speed liquid chromatography as set forth in claim 1, wherein said hollow tubular body is provided with an external tube of stainless steel.

4. A column for use in high speed liquid chromatography as set forth in claim 2, wherein said hollow tubular body is provided with an external tube of stainless steel.

5. A column for use in high speed liquid chromatography as set forth in claim 1, wherein said spherical particles are arranged in multi-layers radially extending, in a fashion that every other layer is repeatedly the same.

* * * * *